(12) United States Patent
Wong et al.

(10) Patent No.: US 9,138,746 B2
(45) Date of Patent: Sep. 22, 2015

(54) FLUID STOP FOR MEASURED SAMPLE CONTAINMENT

(71) Applicant: Honeywell International Inc., Morristown, NJ (US)

(72) Inventors: Pamela Wong, White Bear Lake, MN (US); Lynn Seifried, Minneapolis, MN (US)

(73) Assignee: Honeywell International Inc., Morristown, NJ (US)

( * ) Notice: Subject to any disclaimer, the term of this patent is extended or adjusted under 35 U.S.C. 154(b) by 99 days.

(21) Appl. No.: 13/874,604

(22) Filed: May 1, 2013

(65) Prior Publication Data

US 2014/0329329 A1  Nov. 6, 2014

(51) Int. Cl.
*B01L 3/00* (2006.01)
*G01N 33/86* (2006.01)
*G01N 33/48* (2006.01)
*G01N 33/49* (2006.01)

(52) U.S. Cl.
CPC ..... *B01L 3/502753* (2013.01); *B01L 3/502723* (2013.01); *G01N 33/86* (2013.01); *B01L 2200/0684* (2013.01); *B01L 2300/0816* (2013.01); *B01L 2300/0883* (2013.01); *G01N 33/491* (2013.01); *Y10T 436/2575* (2015.01); *Y10T 436/25375* (2015.01)

(58) Field of Classification Search
CPC . B01L 3/502; B01L 3/5027; B01L 3/502715; B01L 3/502723; B01L 3/502753; B01L 3/502761; B01L 2200/027; B01L 2200/0605; B01L 2200/10; B01L 2200/0684; B01L 2300/0816; B01L 2300/0861; B01L 2300/087; B01L 2300/0883; G01N 1/18; G01N 1/34; G01N 21/03; G01N 21/11; G01N 33/48; G01N 33/49; G01N 33/491; Y10T 436/25; Y10T 436/25375; Y10T 436/255; Y10T 436/2575
USPC ............. 436/63, 69, 164, 165, 174, 175, 177, 436/178, 180; 422/400, 401, 408, 412, 414, 422/417, 73, 82.05, 501, 502, 503, 507, 422/527, 534, 535, 551, 552, 554
See application file for complete search history.

(56) References Cited

U.S. PATENT DOCUMENTS

| 8,309,040 B2 | 11/2012 | Chung et al. | |
| 2006/0269978 A1* | 11/2006 | Haworth et al. | 435/13 |
| 2012/0058500 A1* | 3/2012 | Mitchell et al. | 435/13 |

(Continued)

FOREIGN PATENT DOCUMENTS

| EP | 1412065 A2 | 4/2004 |
| EP | 1441131 A1 | 7/2004 |

(Continued)

OTHER PUBLICATIONS

"European Application Serial No. 14164821.2, Extended European Search Report mailed Jun. 9, 2015", 3 pages.

(Continued)

*Primary Examiner* — Maureen Wallenhorst
(74) *Attorney, Agent, or Firm* — Schwegman Lundberg & Woessner, P.A.

(57) ABSTRACT

A test cartridge includes an input channel to receive a liquid sample to be tested. A sample chamber is coupled to the input channel to receive the sample. An air permeable membrane is coupled between the sample chamber and ambient to prevent passage of the sample past the membrane and stop movement of the sample in the sample chamber.

20 Claims, 2 Drawing Sheets

(56) References Cited

U.S. PATENT DOCUMENTS

| | | |
|---|---|---|
| 2012/0220047 A1* | 8/2012 | Seifried et al. ............... 436/178 |
| 2012/0228142 A1 | 9/2012 | Sibbett et al. |
| 2013/0083311 A1* | 4/2013 | Li et al. ........................ 356/39 |
| 2014/0087359 A1* | 3/2014 | Njoroge et al. ................. 435/2 |

FOREIGN PATENT DOCUMENTS

| | | |
|---|---|---|
| EP | 2344883 A2 | 7/2011 |
| EP | 2492682 A1 | 8/2012 |
| EP | 2504105 A1 | 10/2012 |
| WO | WO-03/076937 A2 | 9/2003 |
| WO | WO-2007/005973 A2 | 1/2007 |
| WO | 2010/120786 * | 10/2010 |

OTHER PUBLICATIONS

"European Application Serial No. 14164821.2, Examination Notification Art. 94(3) mailed Jun. 26, 2015", 6 pages.

\* cited by examiner

FLUID STOP FOR MEASURED SAMPLE CONTAINMENT

BACKGROUND

Microfluidic test cartridge s for use in test instruments are used to process samples, such as blood samples and transport the processed samples to areas on the cartridge for the performance of one or more tests. The amount of sample, such as in the case of blood may be limited. Movement of the sample through the cartridge during processing can be difficult to track and stop at an appropriate time.

To determine the percent activation energy of an individual's platelet sample, the images of a single plasma sample, in two different conditions is taken and analyzed. One plasma condition includes untreated platelet rich plasma (PRP) condition of a blood sample taken from a patient (baseline state), while a second plasma condition is observed after exposure (and shear) to an agonist. In order to image the platelets clearly, everything in imaging windows of the microfluidic cartridge should be stable (both plasma and platelets in the plasma). In previous methods, a sample would have to be manually stopped by turning off the pump. The sample would continue to flow past the stopping point while, wasting time waiting for equilibrium to be reached in the microfluidic cartridge. The lesser results were that the shear rate was not known and the time to stop the sample varied, but more often the sample would be pushed completely out the microfluidic cartridge.

Other prior devices include an LTA (light transmission agregometer), using two physically different platelet samples from a patient. The light transmission of the untreated sample would be measured and then the agonist would be added to the $2^{nd}$ sample, the sample sheared and, while shearing, the transmitted light would be measured through the sample tube. As the platelets aggregated, the amount of light transmitted through the tube would decrease, but as they reached a critical size and dropped down to the bottom of the tube, more light would be transmitted through the tube. The test would typically take about 10 minutes.

Other methods include using electronic measurements to measure the conductivity across a platelet sample. Two platelet samples were required, such as the Mindray (Helena) method. The problem with these methods is that hand shear is done by shaking the sample tube, repeatably from sample to sample which is extremely difficult to do.

SUMMARY

A test cartridge includes an input channel to receive a liquid sample to be tested. A sample chamber is coupled to the input channel to receive the sample. An air permeable membrane is coupled between the sample chamber and ambient to prevent passage of the sample past the membrane and stop movement of the sample in the sample chamber.

In a further embodiment, a test cartridge includes a shear channel formed to receive a plasma sample containing platelets, to trap the platelets, and to provide an aggregated plasma sample. A sample chamber is coupled to the shear channel to receive the aggregated plasma sample. An air permeable membrane is coupled between the sample chamber and ambient to prevent passage of the aggregated sample past the membrane.

In yet a further embodiment, a test cartridge includes an input channel to receive a sample containing platelets, a first sample chamber coupled to the input channel to receive the sample containing platelets, a shear channel coupled to the first sample chamber to receive the sample containing platelets and to trap the platelets, a second sample chamber coupled to the shear channel to receive the sample without the trapped platelets, and an air permeable membrane coupled between the second chamber and ambient to prevent passage of the sample past the membrane.

A method including receiving a plasma sample, using pressure to move the plasma sample through a shear channel to remove platelets form the plasma sample, providing the plasma sample following removal of the platelets to a second sample test chamber, and stopping the flow of plasma past the sample test chamber via an air permeable membrane.

DETAILED DESCRIPTION

Figure 1:
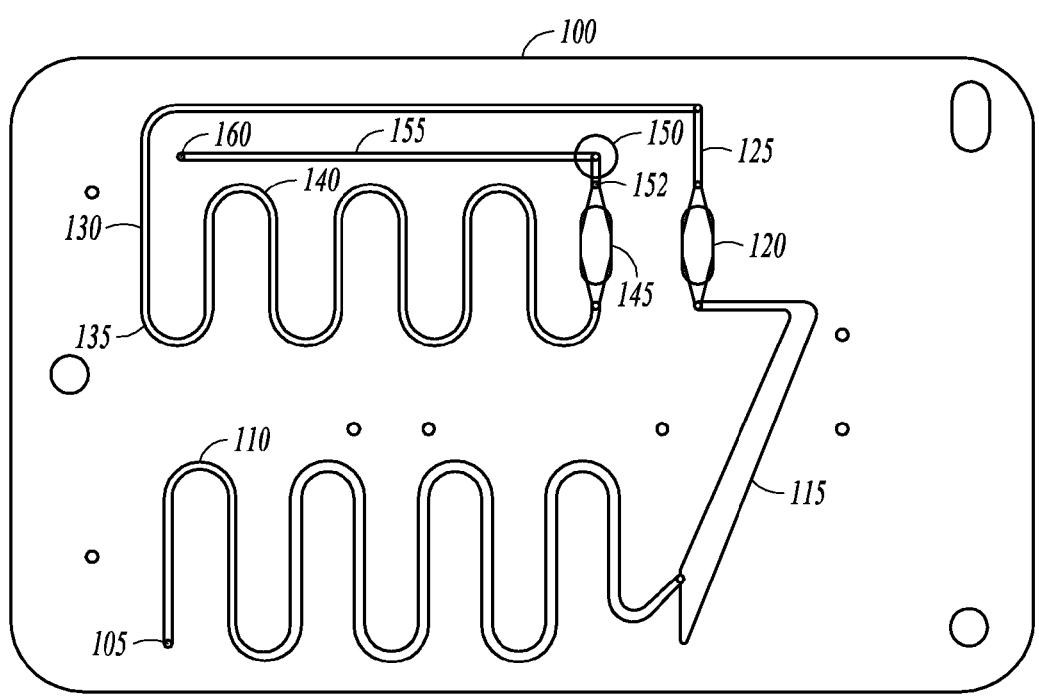
FIG. 1 is a top view of a multilayer test cartridge according to an example embodiment.

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

In various embodiments of a microfluidic test card or cartridge, a gas permeable membrane is placed a short distance from an end of an imaging window. This gas permeable membrane allows air to leave the cartridge while a sample being tested, such as plasma travels through the cartridge. The sample in some embodiments may react with an agonist and undergo shearing to activate platelets and fill one or more imaging windows. When plasma "hits" the gas permeable membrane, all forward momentum on the platelets and plasma ends and the platelets remain stationary. This sudden cessation of forward movement ensures that each sample tested is prepared repeatably, and enables quick imagining of platelets in the imaging windows even though the cartridge is moved quickly between and across the imaging windows. Percent activation calculations may be completed in a timely manner (in less than half the time currently required by the gold standard light transmission agrogometry).

A further advantage of some embodiments is that a single sample may be provided to the microfluidic cartridge, allowing images (and calculations) of the same sample, but in different conditions. In one configuration, a front part of the fluid stream contains the activated platelets while a "back end" of the fluid stream, in an unactivated platelet window, contains platelets that have not been exposed to the agonist.

In further embodiments, the use of the gas permeable membrane may aid development of further imaging and corresponding analysis techniques. The gas permeable membrane may be used to quickly stop cell movement in whole blood in order to perform cell counts and identification. The ability to quickly stop cell movement eliminates the need to time the process, and further ensures that a sample will not empty from a window prior to imaging. Further uses may include identification of the presence of "bugs", bacteria, virus, parasites, etc. in human fluid samples, or other types of samples.

In further embodiments, two samples in a test cartridge are measured by a test system holding the cartridge to calculate percent aggregation. One sample is an un-aggregated platelet rich plasma (PRP), and the other sample an aggregated sample of PRP. These samples are pushed or pulled through one or more channels adapted to stop flow of the sample at a predefined point so that the accuracy of the samples are not compromised.

A gas permeable membrane may be placed at an end of the channel past the aggregated sample to provide an abrupt stop for the sample. This allows for the sample to be sheared for a known time at a known rate. The percent aggregation can then be calculated. Previously a sample would have to be manually stopped and the sample would continue to flow past the stopping point. The shear rate was not known and the time to stop the sample varied.

In various embodiments, the channels may be cut using a $CO_2$ laser and laminated to form the test cartridge. A plasma sample is loaded into the cartridge and pulled or pushed through one or more channels. The sample is then stopped at the gas permeable membrane and continues into a measurement area to be interrogated by a test system adapted to receive the cartridge. The test system may have one or more radiation sources, such as light emitting diodes (LEDs) and detectors positioned to provide and detect radiation to and from sample chambers in the cartridge.

FIG. 1 is a top view of a test cartridge 100. In some embodiments, the test cartridge 100 contains many layers of a transparent material such as PET or other acrylic or suitable material that can be patterned with various liquid fluid transport features and laminated to form the text cartridge. The cartridge 100 in some embodiments may be used to perform one or more blood tests utilizing a small volume of blood. The blood or other liquid to be tested, may be transported via one or more layers of the test cartridge, and prepared for analysis by a test instrument into which the cartridge is inserted. Various sensors, such as a combination of light emitting diodes, lasers, and photoreceptors may be used to test the liquid.

In one embodiment, a plasma sample is provided to an input 105 of an input channel 110. The input channel 110 in one embodiment is approximately 1 mm in width, and winds in a serpentine pattern to provide sufficient length to remove air from the sample as the sample is moved by either positive of negative pressure.

In one embodiment, the input channel 110 provides the sample to an elongated chamber or channel 115 that provides sufficient length and width to settle out the sample. The elongated chamber 115 may be several mm in width, and may include a portion that extends below the point at which the input channel empties into the elongated chamber 115.

The elongated chamber 115 provides the settled sample to a first test chamber or cuvette 120. The sample in this chamber contains platelets. The sample then exits via a channel 125 to a shear channel 130. The shear channel 130 traverses the cartridge 100 in a serpentine manner and at least portions of it have a herring bone pattern 135 that contains physical structures that help trap platelets, removing them from the sample. A reagent 140 may be a dried reagent that coats the shear channel 130 and mixes with the sample. Example reagents include ADP and other common platelet aggregators. The shear channel 130 serves as an aggregator, removing platelets from the sample to deliver a post aggregated plasma sample to a second test chamber or cuvette 145. In one embodiment the shear channel is approximately 0.5 mm in diameter.

Following the test chamber 145, an air permeable membrane 150 is positioned at an end of a channel 152 in one layer of the multiple layer cartridge 100 and between the end of the channel 152 and an exit channel 155 which exits to ambient, and is formed in a separate layer, which may be adjacent to the layer containing channel 152 or separated by one or more layers with openings to couple the channels.

Figure 2:
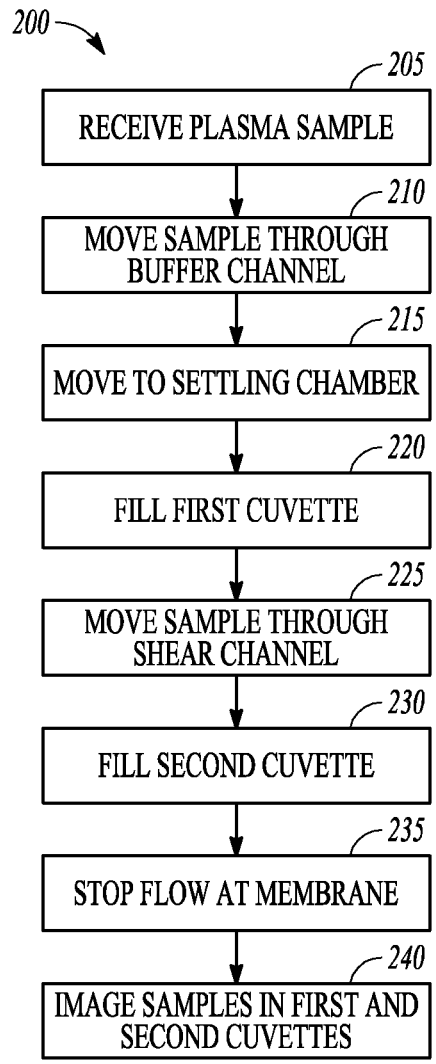
FIG. 2 is a flowchart illustrating a method of moving a plasma sample through channels of a test cartridge according to an example embodiment.

FIG. 2 is a flowchart describing the movement and process 200 of moving a plasma sample through a test cartridge. At 205, a plasma sample is received. In some embodiments, the plasma sample is moved 210 through a buffer channel to remove air from the sample. Negative or positive pressure may be used to move the sample through the test cartridge in various embodiments. The sample may then be moved at 215 to a settling chamber to settle the sample.

At 220, the sample is moved into a first test cuvette to provide an unaggregated sample for measurement. From there, the sample is moved at 225 through a shear channel to remove platelets. Following the shear channel, an aggregated sample is provided at 230 to a second cuvette. Finally, an air permeable membrane is used to stop flow of the sample at 235. The movement of the sample through the various fluidic structures results in an unaggregated, platelet rich plasma sample residing in the first cuvette, and an aggregated plasma sample residing in the second cuvette. The air permeable membrane serves to stop the flow of sample, providing a fixed time for shearing the sample and ensuring the appropriate samples are provided in the test cuvettes for testing the percentage of aggregation when the cartridge is inserted into a test system and the samples are imaged at 240. In various embodiments, insertion into the test system provides a difference in pressure to move the sample as described in method 200.

Figure 3:
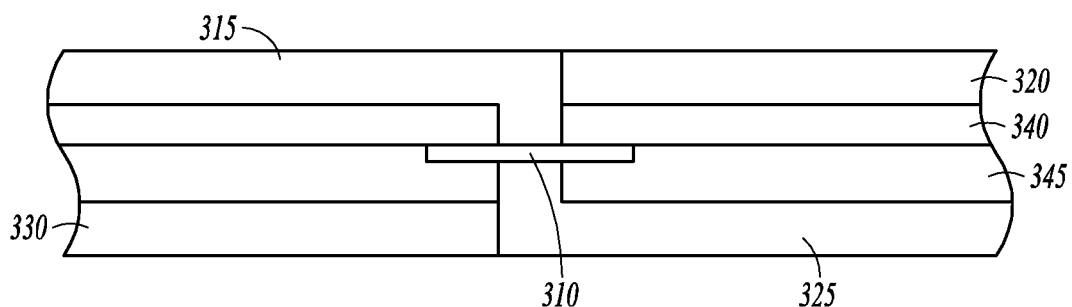
FIG. 3 is a cross section representation of a filter disposed between two channels in separate layers according to an example embodiment.

FIG. 3 is a cross section representation 300 of a filter 310 disposed between an input channel 315 formed in an input channel layer 320, and an output channel 325 formed in an output channel layer 330. The filter 310 in one embodiment is sandwiched between layers indicated at 340 and 345. Layer 340 separates the input channel layer 320 from the filter and includes a throughhole for the input channel 315 such that fluid in the input channel 315 encounters an upstream side of the filter 310. A downstream side of the filter 310 is coupled via a through hole in a layer 345 to couple to the output channel 325, which vents to ambient, such as atmosphere.

Although a few embodiments have been described in detail above, other modifications are possible. For example, the logic flows depicted in the figures do not require the particular order shown, or sequential order, to achieve desirable results. Other embodiments may be within the scope of the following claims.

The invention claimed is:

1. A test cartridge comprising:
    an input channel to receive a sample containing platelets;
    a first test cuvette coupled to the input channel to receive the sample containing platelets;
    a serpentine shear channel coupled to the first test cuvette to receive the sample containing platelets and to trap the platelets;
    a second test cuvette coupled to the shear channel to receive the sample without the trapped platelets; and
    an air permeable membrane coupled between the second test cuvette and ambient to prevent passage of the sample past the membrane and positioned to provide a fixed shear time in the serpentine shear channel.

2. The test cartridge of claim 1 wherein the shear channel contains a platelet aggregating reagent.

3. The test cartridge of claim 1 wherein the shear channel contains structural features to trap the platelets.

4. The test cartridge of claim 3 wherein the structural features comprise a herring bone pattern.

5. The test cartridge of claim 4 wherein the shear channel is formed in a serpentine shape in a single layer of the test cartridge.

6. The test cartridge of claim 1 wherein the first and second test cuvettes are positioned proximate each other on the test cartridge to facilitate optical based testing.

7. The test cartridge of claim 1 and further comprising an exit channel coupled between the air permeable membrane and ambient.

8. The test cartridge of claim 7 wherein the membrane is positioned between different layers of the test cartridge, with the shear channel and exit channel being formed in the different layers.

9. The test cartridge of claim 1 and further comprising an elongated chamber coupled between the input channel and the first test cuvette, the elongated chamber formed to settle out platelets in the sample.

10. The test cartridge of claim 9 wherein the input channel comprises a buffer channel to remove air from the channel and wherein the input channel is coupled to the elongated chamber above a low point in the elongated chamber.

11. A test cartridge comprising:
an input channel to receive a liquid sample containing platelets to be tested;
a test cuvette coupled to the input channel to receive the sample;
a serpentine shear channel coupled between the input channel and the test cuvette to receive the sample containing platelets and to trap the platelets; and
an air permeable membrane coupled between the test cuvette and ambient to prevent passage of the sample past the membrane and stop movement of the sample in the test cuvette and positioned to provide a fixed shear time in the serpentine shear channel.

12. The test cartridge of claim 11 wherein the sample comprises a plasma sample and wherein the shear channel contains a reagent.

13. The test cartridge of claim 12 wherein the shear channel contains structural features to trap the platelets.

14. The test cartridge of claim 13 wherein the structural features comprise a herring bone pattern.

15. The test cartridge of claim 14 wherein the shear channel is formed in a serpentine shape in a single layer of the test cartridge.

16. The test cartridge of claim 11 and further comprising an exit channel coupled between the air permeable membrane and ambient.

17. The test cartridge of claim 16 wherein the membrane is positioned between different layers of the test cartridge.

18. A method comprising:
receiving a plasma sample having platelets;
using pressure to move the sample through a serpentine shear channel;
removing platelets from the plasma as it moves through the serpentine shear channel;
providing the sample from the serpentine channel to a test cuvette; and
stopping the flow of plasma past the test cuvette via an air permeable membrane positioned to provide a fixed shear time in the serpentine shear channel.

19. The method of claim 18 including mixing a reagent with the plasma sample as the plasma sample moves through the serpentine shear channel.

20. The method of claim 19 and further comprising providing the plasma sample to a further test cuvette prior to removal of the platelets.

* * * * *